United States Patent [19]
Wakabayashi

[11] Patent Number: 6,146,393
[45] Date of Patent: Nov. 14, 2000

[54] EXTERNAL TUBULAR STAPLING DEVICE FOR ANASTOMOSING A VASCULAR GRAFT TO AN ANASTOMOSING SHEATH

[76] Inventor: Akio Wakabayashi, 16300 Sand Canyon Ave., Irvine, Calif. 92618

[21] Appl. No.: 09/216,200

[22] Filed: Dec. 18, 1998

[51] Int. Cl.<sup>7</sup> ...................................................... A61B 17/00
[52] U.S. Cl. ............................................. 606/153; 606/139
[58] Field of Search ................................ 606/1, 144, 149, 606/150, 151, 153, 154, 139, 219

[56] References Cited

U.S. PATENT DOCUMENTS

| | | |
|---|---|---|
| 2,935,068 | 5/1960 | Donaldson . |
| 4,154,241 | 5/1979 | Rudie . |
| 4,366,819 | 1/1983 | Kaster . |
| 4,368,736 | 1/1983 | Kaster . |
| 4,505,414 | 3/1985 | Filipi . |
| 4,523,592 | 6/1985 | Daniel . |
| 4,553,542 | 11/1985 | Schenck et al. . |
| 4,598,712 | 7/1986 | Rebuffat et al. . |
| 4,650,486 | 3/1987 | Chareire . |
| 4,657,019 | 4/1987 | Walsh et al. . |
| 4,747,407 | 5/1988 | Liu et al. . |
| 4,747,818 | 5/1988 | Edelschick . |
| 4,930,674 | 6/1990 | Barak . |
| 4,931,057 | 6/1990 | Cummings et al. . |
| 4,966,602 | 10/1990 | Rebuffat et al. . |
| 5,188,638 | 2/1993 | Tzakis . |
| 5,222,963 | 6/1993 | Brinkerhoff et al. . |
| 5,267,940 | 12/1993 | Moulder . |
| 5,392,979 | 2/1995 | Green et al. . |
| 5,403,333 | 4/1995 | Kaster et al. . |
| 5,425,761 | 6/1995 | Lundgren . |
| 5,437,684 | 8/1995 | Calabrese et al. . |
| 5,443,198 | 8/1995 | Viola . |
| 5,456,714 | 10/1995 | Owen . |
| 5,993,468 | 11/1999 | Rygaard ..................................... 606/153 |

*Primary Examiner*—Michael Buiz
*Assistant Examiner*—William Lewis
*Attorney, Agent, or Firm*—Willie Krawitz

[57] ABSTRACT

An external tubular vascular stapling device is provided for anastomosing a vascular graft to an anastomosis sheath, the latter being initially attached to an arterial or aortic wall, followed by a secondary anastomosis of the sheath to the vascular graft. The procedure enables the device and method to obviate the need for arterial occluding clamps, and produces a stable anastomosis connection. A suitable anastomosing device for this procedure comprises a stapler housing and a separate, multi-grooved anvil which when assembled, form double aligned tubes. The stapling housing includes staple wires and staple pushers mounted within slots oriented orthogonally to the anvil grooves, the vascular graft, and the anastomosis sheath. The distal end of the vascular graft is passed through the tubular portion of the anvil and everted over the end of the anvil. The proximal end of the graft is either tied off or temporarily cross-clamped with vascular clamps. The staple wires are then bent over the anvil by the staple pushers to effect anastomosis of the graft and the sheath, followed by withdrawing the device. This new method and apparatus facilitates an endoscopic vascular anastomosis by eliminating the need for vascular clamps that obstruct endoscopic viewing, interfere with endoscopic maneuvering in a limited area, and whose use may cause tissue injury downstream of the anastomosis site due to lack of an adequate blood supply.

10 Claims, 5 Drawing Sheets

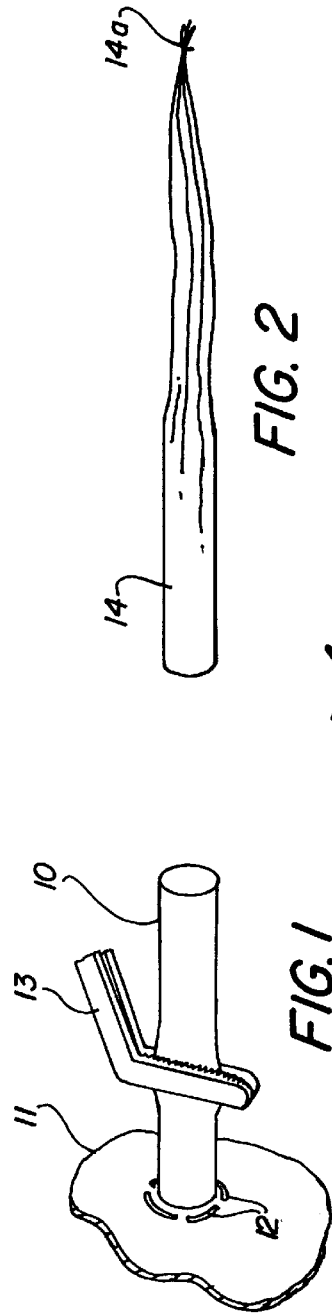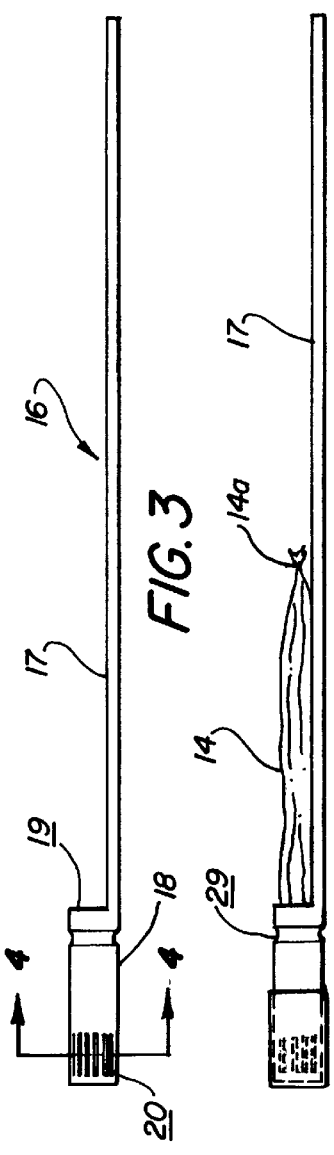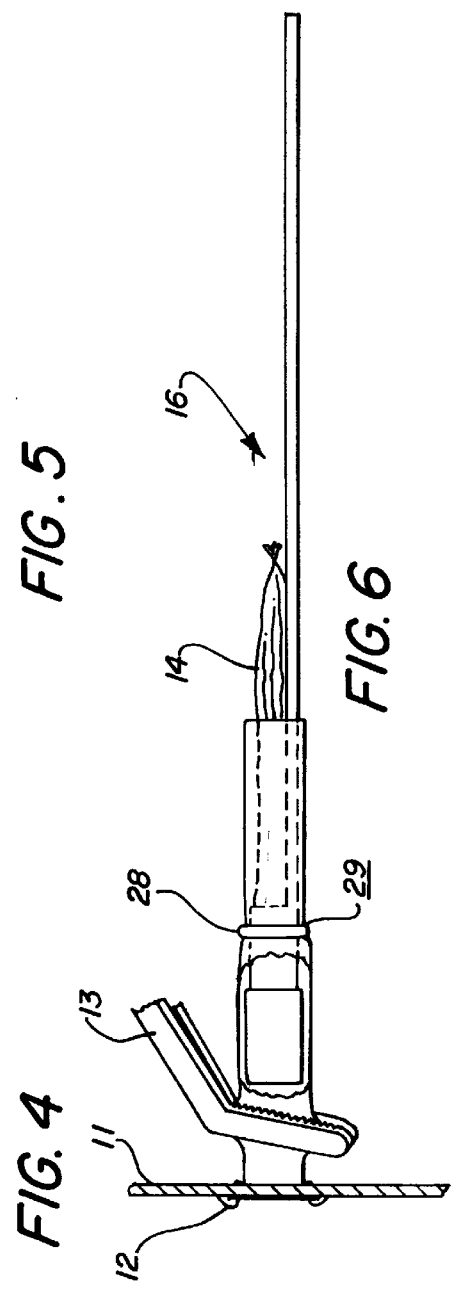

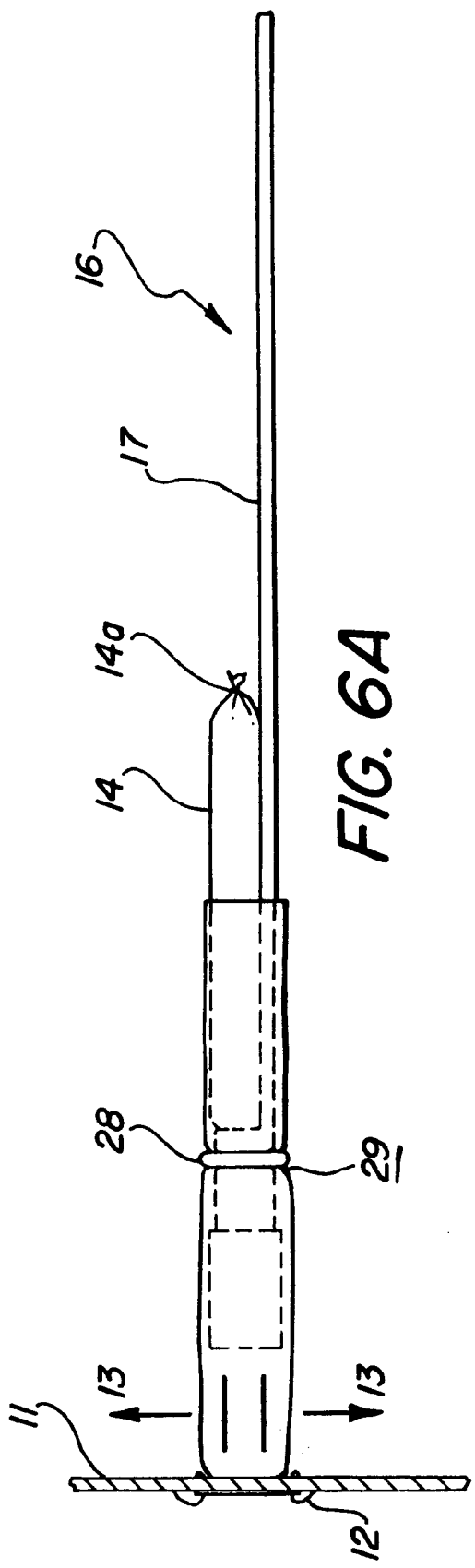

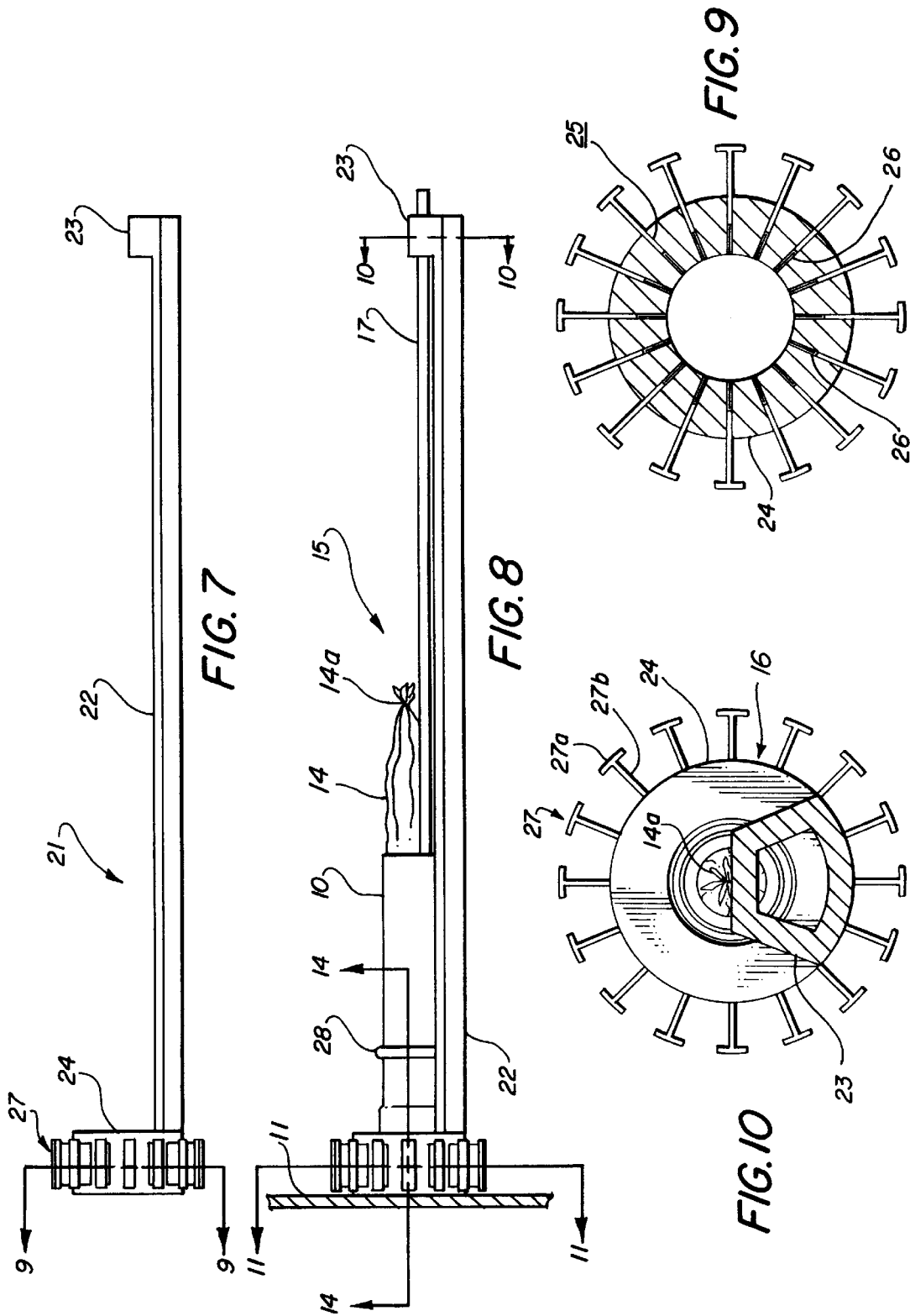

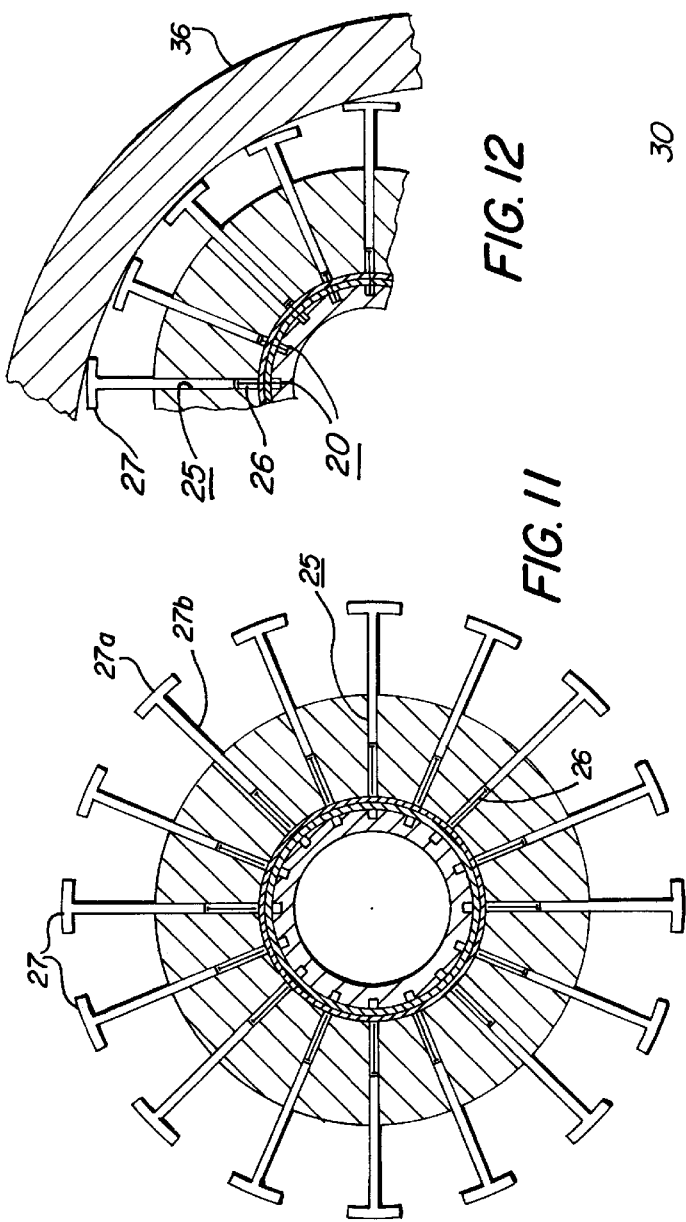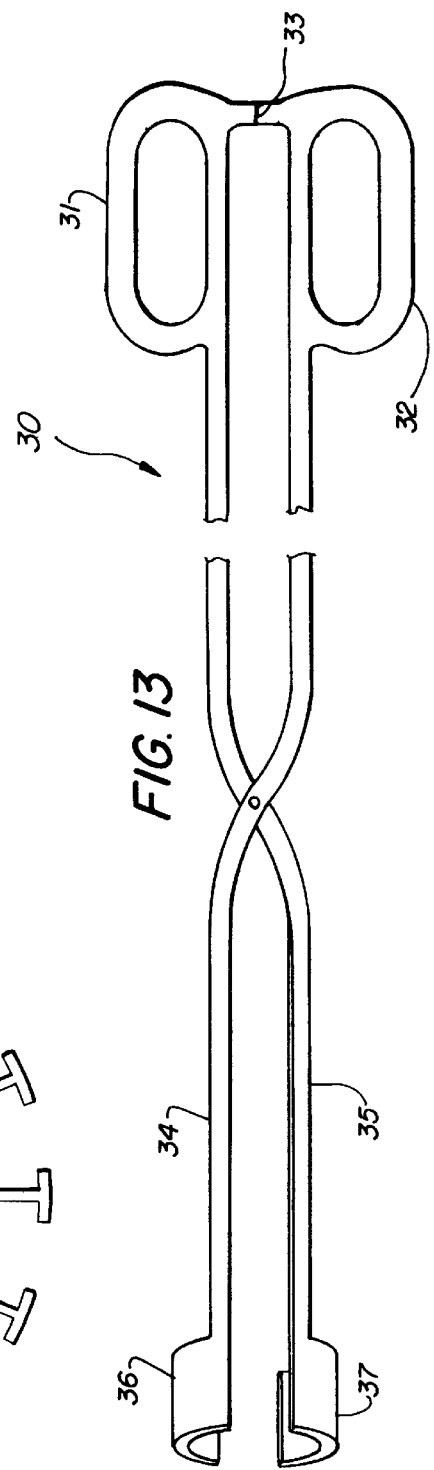

EXTERNAL TUBULAR STAPLING DEVICE FOR ANASTOMOSING A VASCULAR GRAFT TO AN ANASTOMOSING SHEATH

BACKGROUND OF THE INVENTION

This invention relates to a new and improved surgical device and method for end-to-side vascular anastomosis without requiring vascular clamps that constitutes a part of by-pass procedures and a new apparatus comprising an external tubular stapler for connecting a by-pass vascular graft to an anastomosing sheath.

The use of vascular clamps poses difficulties during an endoscopic anastomosis due to the small space available for maneuvering the various surgical instruments employed in this procedure. There is also a possibility of inadvertently injuring the arteriosclerotic arterial or aortic wall when using partial vascular clamps. The apparatus and method of this invention have particular use in conjunction with Applicant's application, entitled: "END-TO-SIDE VASCULAR ANASTOMOSING STAPLING DEVICE"; Ser. No. 09/033,035; filed: Mar. 21, 1998, now U.S. Pat. No. 5,951,576.

Typical publications describing these procedures are described in U.S. Pat. Nos. 2,935,068; 4,154,241; 4,366,819; 4,368,736; 4,505,414; 4,523,592; 4,553,542; 4,598,712; 4,650,486; 4,657,019; 4,747,407; 4,747,818; 4,930,674; 4,931,057; 4,966,602; 5,188,638; 5,222,963; 5,267,940; 5,392,979; 5,403,333; 5,425,761; 5,437,684; 5,443,198; 5,456,714.

However, these patents do not provide a method and/or equipment for performing a vascular anastomosis without temporarily occluding an artery or aorta, partially or totally, and which would be suited for endoscopic vascular end-to-side anastomosis. Hence, a method and/or equipment are desired which can be applied to a by-pass procedure in general, and to an anastomosis procedure in particular. Additionally, a procedure and means are desired which provide a strengthened connection between a by-pass graft and a vein or artery, irrespective of the type of by-pass equipment (employed, and which would be useful, particularly in confined spaces or with a small vein or artery.

Additionally, it is desired to provide an apparatus and method for end-to-side anastomosis of a coronary artery by-pass graft without requiring a heart-lung apparatus and associated equipment, such as a blood oxygenator. Also, it is desired to provide a method and/or equipment which eliminates a partial or total vascular clamping procedure. Since a considerable period of time may be consumed when sewing or stitching is employed for anastomosing a vascular graft with a coronary artery, a total vascular clamping procedure during this time period may jeopardize tissues downstream from the clamping site due to lack of an adequate blood supply.

THE INVENTION

According to the invention, there is provided a vascular stapler which may be employed in conjunction with an anastomosing sheath and method, comprising initially attaching an anastomosing tubular sheath to an arterial or aortic wall by an end-to-side tubular stapler followed by tubularly aligning a vascular graft to the sheath and anastomosing the graft and sheath by stapling.

The stapler of this invention which is preferably employed for this procedure comprises an anvil, the distal end of which provides a plurality of multiple grooves arranged in a circular fashion and parallel to the longitudinal axis of the anvil. A staple pusher is provided to move along the anvil and supply staples for insertion into each groove for subsequent stapling together of the vascular graft and anastomosing sheath.

Upon completion of the anastomosing procedure, the staple pusher and anvil are removed, leaving the vascular graft attached securely on the anastomosing sheath. The other end of the vascular graft may be anastomosed to a second anastomosing sheath that had been previously attached to a second artery or aorta, such as in Applicant's Ser. No. 09/033,035, supra, in a similar fashion, thus completing the by-pass procedure.

BRIEF DESCRIPTION OF THE DRAWINGS

FIG. 1 is a perspective view of an anastomosing sheath element attached to the wall of an artery or aorta;

FIG. 2 is an external view in side elevation of a vascular graft suitable for anastomosis with the sheath element;

FIG. 3 is an external view in side elevation of the anvil portion of the stapler of this invention;

FIG. 4 is a sectional view of the anvil, taken along lines 4—4 of FIG. 3 and showing the grooves along which staples are pressed;

FIG. 5 is an external view in side elevation showing the tied-off, vascular graft which has been everted over the anvil;

FIG. 6 is an external view in side elevation, and partly in section, showing the anvil and the vascular graft inside the anastomosing sheath;

FIG. 6A is an external view in side elevation and partly in section, showing the vascular graft secured inside the sheath by an elastic band to form a water-tight assembly;

FIG. 7 is an external view in side elevation showing the staple pusher portion of the stapling device;

FIG. 8 is an external view of the assembled stapler comprising the anvil, staple pusher, anastomosing sheath and vascular graft prior to anastomosing with the sheath;

FIG. 9 is a cross section view in end elevation taken along lines 9—9 of FIG. 7, showing staple compression pins and staples prior to compression in an anastomosing procedure;

FIG. 10 is a cross section view in axial section taken along lines 10—10 of FIG. 8, and showing the staple compression pins in the background;

FIG. 11 is an enlarged cross section view in axial section taken along lines 11—11 of FIG. 8 showing the assembled stapler prior to anastomosing with the sheath;

FIG. 12 is an enlarged view showing a portion of a staple compression tool acting on a section of staple compression pins and staples during an anastomosing procedure;

FIG. 13 is an external view, partly in perspective showing the entire staple compression tool shown in FIG. 12;

DESCRIPTION OF THE PREFERRED EMBODIMENTS

Figure 15:
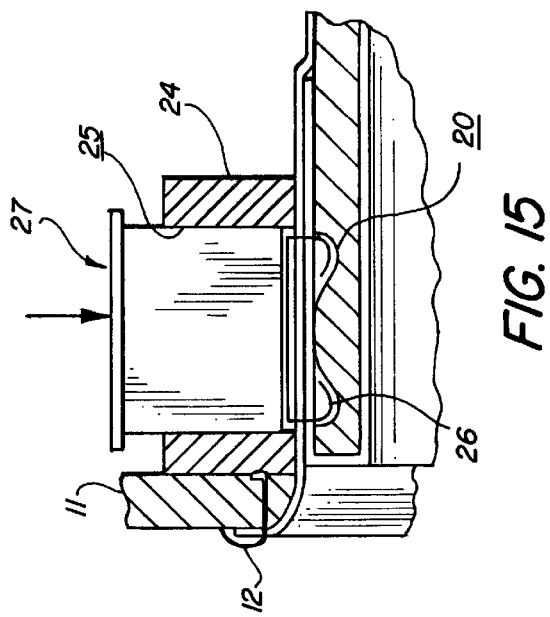
FIG. 15 is an enlarged view in section side elevation of an enlarged portion of FIG. 14 illustrating completion of the anastomosis procedure; and, FIG. 16 is a perspective view showing the anastomosed vascular graft anastomosed to the anastomosing sheath, which in turn is attached to the arterial wall.

An anastomosing sheath 10 is illustrated in FIG. 1 following attachment to an arterial sidewall 11 and connection through an orifice 11a (FIG. 14) by means of staples 12, and clamped off by means of a temporary clamp 13. Use of the sheath provides a secure base for anastomosis with a vascular graft 14 which is end sealed 14a, as shown in FIG. 2, or temporarily cross-clamped.

Materials for the sheath require biocompatability with blood, tissues and fluids, and possess wear and physical properties such as strength, flexibility, permeability and degradation, and might include segmented polyurethanes.

Figure 14:
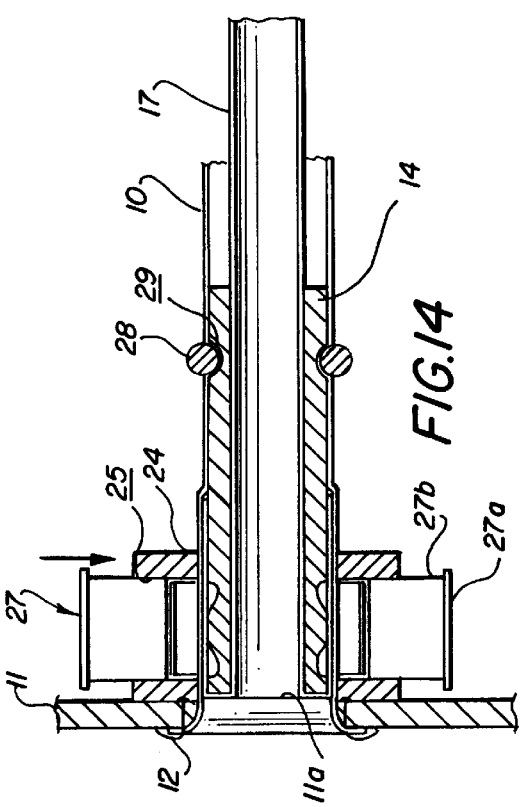
FIG. 14 is a cross section view in side elevation taken along lines 14—14 of FIG. 8 illustrating anastomosis of the sheath with the vascular graft.
Figure 16:
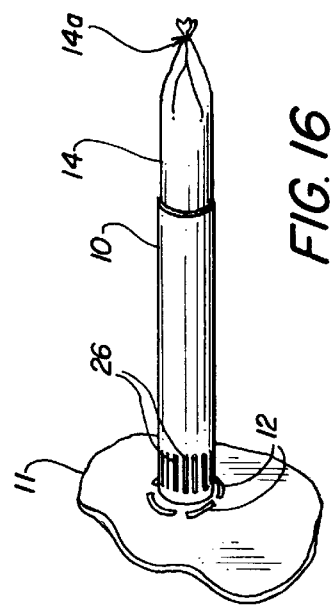

An anvil 16 with the vascular graft 14 shown in FIG. 5 is inserted into the anastomosing sheath 10 shown in FIG. 1. The anvil is sized for back and forth, relatively free movement inside the anastomosing sheath to align the distal end with the base of the anastomosing sheath, or level with the arterial or aortic wall 11, as shown by the arrows in FIG. 6A. This movement permits the end of the anvil to be positioned flush with the arterial or aortic wall, as shown in FIGS. 14, 15 and 16 and enables staples from a tubular anastomosing stapler to anastomose the vascular graft 14 to the sheath 10 and flush with the arterial or aortic wall 11.

As shown in FIG. 10, the anvil 16 includes a handle component 17, which is passed through an opening 23 of a tubular staple pusher 21 which will be described in more detail, infra; and, FIG. 8 shows the tubular portion of the staple pusher aligned with the anvil to a suitable degree of precision.

The assembled stapling device 15 of the invention comprising the anvil 16 and staple pusher 21 are shown in FIG. 8. The anvil itself is shown in FIGS. 3 and 5 and includes an elongate handle 17, and a tubular portion 18 at the distal end defining a central hollow bore 19. External, staple compression grooves 20 are machined around the circumference of the anvil near the distal end of the tubular portion. The staple pusher 21 shown in FIGS. 7–10 provides an elongate portion 22 having a stud bore 23 at the proximal end to align the handle 17 of the anvil. A circular tubular element 24 is formed or mounted at the distal end of the staple pusher, and includes circumferential slots 25 which register with the staple compression grooves 20 of the anvil 16.

Staples 26 are loaded into the interior portion of the slots 25, and staple compression pins 27 defining a head end 27a, and body portion 27b are mounted in the outer portion of the slots. When compressed, the staple compression pins will be driven inwardly along slots 25, thereby contacting and driving the staples into the compression grooves 20 of the anvil, and result in anastomosing the sheath 10 and vascular graft 14.

An occlusive elastic band 28 is applied to the anastomosing sheath over a circular groove 29 near the end of the anvil, and the elastic band prevents blood leakage from a space between the anastomosing sheath and the anvil. Hence, when the clamps 13 on the sheath are released, as shown by the arrows in FIG. 6A, blood from the artery or aorta will instantly fill the sheath and graft; however, blood leakage will be prevented since the elastic band forms a liquid tight seal with the sheath, graft and anvil.

The staple compression pins 27 are compressed by means of a compression tool 30, shown in FIG. 13, the compression tool providing handle grips 31, 32 separated by a closure stop 33. The closure stop prevents excessive pressure being applied to the staples, vascular graft and sheath when the staple compression pins 27 are driven against the staples 26. The handle grips 31 and 32 are integrally formed with connecting arms 34, 35 which terminate at the distal end of the compression tool to provide hemitubular compression segments 36 and 37.

FIG. 12, shows the compression tool 30 being positioned against the compression pins 27 and then partially closed, and the compression segment 36 is shown initially contacting the head end 27a of the pins. This partial closure compresses the body portion 27b of the pins along their respective slots 25 towards their corresponding grooves. FIG. 12 shows only one side of the compression pin assembly, while the opposite side of the pin assembly is similarly contacted by the compression segment 37.

Further closure of the compression tool 30 in FIG. 12 will drive the pins 27 into contact with the staples 26 along their respective slots 25 and move the staples into the grooves 20 of the anvil 16. As shown in FIGS. 14, 15 and 16, additional compression of the staples along the grooves 20 will form the staples into their final shape as they are driven through the vascular graft and sheath, to complete the anastomosis procedure.

The anastomosed sheath with the vascular graft and arterial or aortic wall are shown in FIG. 16 after removing the external tubular stapler. As indicated, supra, the anastomosis procedure will form an open connection between the arterial or aortic lumen via the anastomosing sheath and vascular graft. Hence, when arterial blood enters the sheath, it will fill the vascular graft causing it to expand from the slack forms shown in FIGS. 2, 5, 6, and 8, to becoming filled, as shown in FIGS. 6A and 16.

Following removal of the external tubular stapler, the vascular graft is connected to the artery or aorta via a short segment of the anastomosing sheath such as disclosed in Applicant's patent application, Ser. No. 09/033,035, supra.

The stapling device and method, and use of a sheath connection of this invention simplifies an end-to-side vascular anastomosis which constitutes a component of a by-pass procedure. Also, since anastomosis of the vascular graft to the artery by sewing is replaced by a stapling procedure for anastomosis of the graft to the anastomosing sheath, this eliminates the necessity of employing vascular clamps on the artery or aorta. This in turn greatly prevents inadvertent injury to the arterial or aortic wall, and injury to tissues downstream of the anastomosis site caused by blocking the blood supply. A similar anastomosing procedure between the other end of the graft and an anastomosing sheath previously attached on the recipient artery will complete the by-pass procedure.

What is claimed is:

1. An assembly of a stapling device and a separately functional compression tool for anastomosing a vascular graft to a tubular sheath which has been anastomosed to an aorta or artery, comprising:

a.) an anvil member defining proximal and distal ends, the anvil member providing an elongate handle portion at the proximal end, a tubular anvil portion at the distal end, and a plurality of stapling grooves circumferentially defined on the anvil portion, the tubular portion of the anvil being constructed for insertion into the tubular sheath, the vascular graft being evertable over the distal end of the anvil and adjacent the tubular sheath;

b.) a tubular staple pusher defining a proximal end, and a tubular distal end, the staple pusher providing an alignment means at the proximal end and a plurality of slots circumferentially disposed around the tubular distal end for registration with the stapling grooves, the stapling grooves of the anvil being oriented parallel to a longitudinal axis of the anvil, and the staple pusher slots being oriented perpendicular to the stapling grooves, the tubular portion of the anvil being formed into an assembly with the staple pusher by insertion through the alignment means of the staple pusher, and the tubular distal end of the staple pusher to effect registration of the staple pusher slots with the anvil grooves, the proximal end of the anvil being secured by the alignment means of the staple pusher, thereby stabilizing and aligning the assembly during use; and, c.) a compression tool for simultaneously circumferentially compressing by means of staple compression pins, loaded staples through the slots and into the stapling grooves, for anastomosing the tubular sheath with the vascular graft; whereby, the assembly of the anvil member and staple pusher, and compression tool are configured for separate insertion into an anastomosis site, and following the anastomosing procedure, the anvil member and staple pusher are configured for separate withdrawal from the anastomosis site.

2. The stapling device of claim 1, including resilient clamping means circumferentially disposed around the vascular graft and the tubular sheath during the anastomosis procedure, thereby forming a liquid tight seal.

3. A method for forming a stable connection between an arterial or aortic wall and a by-pass vascular graft, comprising providing a tubular sheath connection, stapling the sheath connection to the arterial or aortic wall to form an end-to-side anastomosis, enclosing the vascular graft within the sheath connection, and anastomosing the sheath connection to the vascular graft by stapling, the sheath connection being biocompatable with blood, tissue and fluids, and providing long term physical properties including strength, flexibility, permeability and resistance to degradation.

4. The method of claim 3, comprising anastomosing the sheath and vascular graft flush with the arterial or aortic wall.

5. A method for anastomosing a vascular graft with a tubular sheath which has been anastomosed to an arterial or aortic wall by a stapling device, comprising:

a.) an anvil member defining proximal and distal ends, the anvil member providing an elongate handle portion at the distal end, and a plurality of stapling grooves circumferentially defined on the anvil portion, the tubular portion of the anvil being insertable into a tubular sheath which has been stapled to the aortic wall to form an end-to-side anastomosis, the vascular graft being evertable over the distal end of the anvil and adjacent the tubular sheath;

b.) a tubular staple pusher defining a proximal end, and a tubular distal end, the staple pusher providing an alignment means at the proximal end, and a plurality of slots circumferentially disposed around the tubular distal end for registration with the stapling grooves, the tubular portion of the anvil being formed into an assembly with the staple pusher by insertion through the alignment means of the staple pusher, and the tubular distal end of the staple pusher to effect registration of the staple pusher slots with the anvil grooves, the proximal end of the anvil being secured by the alignment means of the staple pusher, thereby stabilizing and aligning the assembly during use; and, c.) a compression tool functionally separate from the assembly for simultaneously compressing, by means of staple compression pins, loaded staples through the slots and into the circumferential stapling grooves, the method, comprising:

i. inserting the vascular graft into the tubular portion of the anvil;

ii. everting the vascular graft over the distal end of the anvil and adjacent the tubular sheath to form an anastomosis site;

iii. assembling the anvil member and staple pusher in the anastomosis site;

iv. loading a plurality of staples into the slots;

v. separately inserting the compression tool into the anastomosis site, and compressing loaded staples through the slots and into the circumferential stapling grooves, thereby anastomosing the sheath with the vascular graft; and, vi. separately withdrawing the compression tool and the assembly of the anvil and staple pusher from the anastomosis site following the anastomosis procedure.

6. The method of claim 5, in which the stapling device includes resilient clamping means circumferentially disposed around the vascular graft and the tubular sheath during the anastomosis procedure, thereby forming a liquid tight seal.

7. The method of claim 5, in which the circumferential grooves of the anvil are oriented parallel to the longitudinal axis of the anvil, and the staple pusher slots are oriented perpendicular to the grooves.

8. The method of claim 5, in which the vascular graft and sheath are positioned flush with the anastomosed aortic or arterial wall.

9. The method of claim 5, in which the sheath is biocompatable with blood, tissue and fluids, and providing long term physical properties including strength, flexibility, permeability and resistance to degradation.

10. A method for forming a stable connection between a body member and a by-pass graft, comprising providing a tubular connection, stapling the body member to the tubular connection to form an end-to-side anastomosis, enclosing the by-pass graft with the tubular connection, and anastomosing the tubular connection to the by-pass graft by stapling, the tubular connection being biocompatible with blood, tissue and fluids, and providing long term physical properties including strength, flexibility, permeability and resistance to degradation.

* * * * *